(12) United States Patent
Löptien (10) Patent No.: US 9,765,357 B2
(45) Date of Patent: Sep. 19, 2017

(54) THRIPS RESISTANT CABBAGE

(71) Applicant: RIJK ZWAAN ZAADTEELT EN ZAADHANDEL B.V., De Lier (NL)

(72) Inventor: Harm Löptien, De Lier (NL)

(73) Assignee: Rijk Zwaan Zaadteelt en Zaadhandel B.V., De Lier (NL)

( * ) Notice: Subject to any disclaimer, the term of this patent is extended or adjusted under 35 U.S.C. 154(b) by 768 days.

(21) Appl. No.: 13/799,104

(22) Filed: Mar. 13, 2013

(65) Prior Publication Data

US 2013/0283479 A1  Oct. 24, 2013

(30) Foreign Application Priority Data

Apr. 19, 2012 (EP) .................... 12164775

(51) Int. Cl.
| | |
|---|---|
| *C12N 15/82* | (2006.01) |
| *A01H 1/04* | (2006.01) |
| *A01H 5/10* | (2006.01) |
| *A01H 5/12* | (2006.01) |
| *C07K 14/415* | (2006.01) |
| *C12Q 1/68* | (2006.01) |

(52) U.S. Cl.
CPC ........... *C12N 15/8286* (2013.01); *A01H 1/04* (2013.01); *A01H 5/10* (2013.01); *A01H 5/12* (2013.01); *C07K 14/415* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| 8,993,855 B2 | 3/2015 | Linders et al. |
| 2010/0122383 A1 | 5/2010 | Linders et al. |

FOREIGN PATENT DOCUMENTS

CN  101730750  6/2010

OTHER PUBLICATIONS

Griffiths (Report to the NY IPM Program (2002), pp. 1-8).*
Fail, et al., Developing Methods for Testing the Resistance of White Cabbage Against Thrips Tabaci, Proceedings of the 7th International Symposium on Thyanoptera, (2001), pp. 229-237.
Griffiths, et al., Breeding and Characterization of Thrips Resistance in Cabbage, Report to the NY IPM Program, (2008), pp. 1-7.
Voorrips et al., Plant Traits Associated with Resistance to Thrips Tabaci in Cabbage (*Brasscia olearacea* var capitata; Euphytica (2008), vol. 163, No. 3, pp. 409-415.
Trdan et al., Feeding Damage by Onion Thrips, Thrips Tabaci Lindeman (Thysanoptera: Thripidae), on Early White Cabbage Grown Under Insecticide-Free Conditions; African Entimology, (2005) vol. 13, No. 1, pp. 85-95.

* cited by examiner

*Primary Examiner* — David T Fox
*Assistant Examiner* — Jared Shapiro
(74) *Attorney, Agent, or Firm* — Vedder Price P.C.; Thomas J. Kowalski; Deborah L. Lu (57) ABSTRACT

The present invention relates to a tomato plant (*Solanum lycopersicum* L.) which may comprise a genetic determinant that confers resistance to Pepino Mosaic Virus (PepMV), wherein the resistance is characterised by the presence of at least QTL1 and/or QTL2. The invention also relates to sources for obtaining said genetic determinant, representative seed of which were deposited with the NCIMB under accession numbers NCIMB 41927, NCIMB 41928, NCIMB 42068, and NCIMB 42069. The invention further relates to seeds and progeny of the plant and to its fruits and processed fruits. In addition the invention relates to molecular markers linked to PepMV resistance conferring QTLs and the use thereof.

16 Claims, 1 Drawing Sheet

SEQUENCE LISTING

```
<160> NUMBER OF SEQ ID NOS: 7

<210> SEQ ID NO 1
<211> LENGTH: 121
<212> TYPE: DNA
<213> ORGANISM: Brassica oleracea
<220> FEATURE:
<221> NAME/KEY: source
<222> LOCATION: 1..121
<223> OTHER INFORMATION: /mol_type="DNA"
      /organism="Brassica oleracea"
<220> FEATURE:
<221> NAME/KEY: variation
<222> LOCATION: 61
<223> OTHER INFORMATION: /replace="c"

<400> SEQUENCE: 1
ttgtccggaa aataagccct tccttctcca tgagccgccc aaactcctaa agtacttacc      60
ttccattcct ttcagcacta ttgacggaca gtccttgatg gtcacgcttg tgaacctgca    120
g                                                                    121

<210> SEQ ID NO 2
<211> LENGTH: 104
<212> TYPE: DNA
<213> ORGANISM: Brassica oleracea
<220> FEATURE:
<221> NAME/KEY: source
<222> LOCATION: 1..104
<223> OTHER INFORMATION: /mol_type="DNA"
      /organism="Brassica oleracea"
<220> FEATURE:
<221> NAME/KEY: variation
<222> LOCATION: 61
<223> OTHER INFORMATION: /replace="c"

<400> SEQUENCE: 2
gcttgtccag cttatgagca ttttgtaata catgtttgct tggatggtca aacctgaaaa      60
```
aacacacaag ttcaacaatt ctcagaagat ggataaacct gcag                      104

<210> SEQ ID NO 3
<211> LENGTH: 274
<212> TYPE: DNA
<213> ORGANISM: Brassica oleracea
<220> FEATURE:
<221> NAME/KEY: source
<222> LOCATION: 1..274
<223> OTHER INFORMATION: /mol_type="DNA"
      /organism="Brassica oleracea"
<220> FEATURE:
<221> NAME/KEY: variation
<222> LOCATION: 13,49,50,54,182,183,184,187,193,194,198,211,212,214,217,
      218,219
<223> OTHER INFORMATION: /note="n= any base"
<220> FEATURE:
<221> NAME/KEY: variation
<222> LOCATION: 130
<223> OTHER INFORMATION: /note="deletion"

<400> SEQUENCE: 3
ttaaaaacaa atnatgtttt gttttacctg cttttccctc ttctcgctnn ttgncagctt      60
cttctctctg ttggcgaatc agagccaaac gatctgtaca caaacacaca caagggataa    120
gataatcaaa taggctcatc tggtaacaaa gaaagagaac aagaggtcca ttgttttttt    180
acnnaantcc ttnnttgntt gctcggtttt nncntgnnnc tgcaacctca tgtatcgctc    240
atgagctcgt tgcttctcta gctcctccct gcag                                274

<210> SEQ ID NO 4
<211> LENGTH: 116
<212> TYPE: DNA
<213> ORGANISM: Brassica oleracea
<220> FEATURE:
<221> NAME/KEY: source
<222> LOCATION: 1..116
<223> OTHER INFORMATION: /mol_type="DNA"
      /organism="Brassica oleracea"
<220> FEATURE:
<221> NAME/KEY: variation
<222> LOCATION: 61
<223> OTHER INFORMATION: /replace="c"
<220> FEATURE:
<221> NAME/KEY: variation
<222> LOCATION: 16
<223> OTHER INFORMATION: /note="n=any base"

<400> SEQUENCE: 4
catgtcatct ttcgtnaggt ttgttatttc tatgcctcgt ttgagagctt ccctcaatgg      60
acccatagtt gcatctttca ctaggttctt catgtctgat cccgagtacc ctgcag        116

<210> SEQ ID NO 5
<211> LENGTH: 112
<212> TYPE: DNA
<213> ORGANISM: Brassica oleracea
<220> FEATURE:
<221> NAME/KEY: source
<222> LOCATION: 1..112
<223> OTHER INFORMATION: /mol_type="DNA"
      /organism="Brassica oleracea"
<220> FEATURE:
<221> NAME/KEY: variation
<222> LOCATION: 37
<223> OTHER INFORMATION: /replace="g"

<400> SEQUENCE: 5
ttaaatatgt gaatgctgaa atrtttgttt agcagacgag acacaggaag aagatcatct      60

```
catgttgttc gctctctcag cagagagttt gaagttgcaa gtactcctgc ag                112
```

```
<210> SEQ ID NO 6
<211> LENGTH: 224
<212> TYPE: DNA
<213> ORGANISM: Brassica oleracea
<220> FEATURE:
<221> NAME/KEY: source
<222> LOCATION: 1..224
<223> OTHER INFORMATION: /mol_type="DNA"
      /organism="Brassica oleracea"
<220> FEATURE:
<221> NAME/KEY: variation
<222> LOCATION: 84
<223> OTHER INFORMATION: /replace="c"

<400> SEQUENCE: 6
ccctgttwaa ggagcctcct tggagcttgt tgatacctca aagttaggta gtgacaatgt        60
ggataatgaa agtttgaagc tttatcaaca attagctgat aagagaggtt cttgtgaaga       120
ggatttgatg agaatctcta tgaagaaacg aggtgtaatc agcaatgtct ccacctctyt       180
gatggaarat gctrgtttyg atggaatatt ggcttctcct gcag                        224

<210> SEQ ID NO 7
<211> LENGTH: 121
<212> TYPE: DNA
<213> ORGANISM: Brassica oleracea
<220> FEATURE:
<221> NAME/KEY: source
<222> LOCATION: 1..121
<223> OTHER INFORMATION: /mol_type="DNA"
      /organism="Brassica oleracea"
<220> FEATURE:
<221> NAME/KEY: variation
<222> LOCATION: 61
<223> OTHER INFORMATION: /replace="g"

<400> SEQUENCE: 7
taaagaacct gatgaagaaa gtgaagagct aggtggaaac ctacttgacc tgctcctaag        60
tttcttcact tccgggatct tctcctcttt tgatctcacc tgcctcacct ttgcctcgtt       120
c                                                                      121
```

US 9,765,357 B2

THRIPS RESISTANT CABBAGE

RELATED APPLICATIONS AND INCORPORATION BY REFERENCE

This application claims benefit of European patent application Serial No. 12164775.4 filed 19 Apr. 2012.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to *Brassica* plants, in particular *Brassica oleracea* plants resistant to *Thrips tabaci*, to seeds and progeny from the seeds and plants, and to a method for producing such a plant.

BACKGROUND OF THE INVENTION

The present invention relates to *Brassica* plants, in particular *Brassica oleracea* plants which are resistant to *Thrips tabaci* and herein display agronomically desirable traits.

*Thrips tabaci* (also known as Onion thrips, or simply thrips) is a highly polyphagous insect and considered as an economically harmful pest for many cultivated crops especially for crops from the Liliaceae, Solanaceae, and Brassicaceae plant families, such as onion, leek, tomato, cabbage, but also in crops from outside these families, such as e.g. cucumber, melon and snap beans (Toda & Murai, 2007, Applied Entomology and Zoology 42: 309-316; Trdan et al., 2005, African Entomology 13: 85-95).

Thrips harm the plant directly by feeding on the plant tissue and indirectly by being a vector for lethal plant viruses such as tomato spotted wild virus (Toda & Murai, 2007, Applied Entomology and Zoology 42: 309-316). Thrips occur worldwide and due to climate change and trade the frequency of thrips infestation is increasing (Trdan et al., 2005; African Entomology 13: 85-95).

Cabbage plants (*Brassica oleracea* var. *capitata* L.) belong to the plant family Brassicaceae. The family has a cosmopolitan distribution and consists of approximately 3500 to 4000 species. The family and especially the genus *Brassica* contains many agronomically important crops such as broccoli, Brussels sprouts, cauliflower, Chinese cabbage, curly cabbage, kale, kohlrabi, mustard, oxheart cabbage, radish, rapeseed, red cabbage, Savoy cabbage, turnip, and white cabbage.

In tissue of *Brassica oleracea* var. *capitata* plants affected by thrips callus growths will form. Over time these callus growths become brown making it necessary to remove several layers of leaves from the cabbage head before marketing. Even in storage the development of symptoms caused by thrips may increase. The reduction in head size and weight ultimately leads to a loss in yield. For *Brassica oleracea* var. *capitata* it is estimated that 75% of its total acreage suffers from thrips.

Controlling thrips in cabbage by means of applying insecticide is considered environmentally unfriendly and ineffective, because the closed leaves of the cabbage heads provide protection to the thrips, and because thrips are hard to detect, sometimes even only at harvest stage. Thrips infestation in cabbages may occur from the second exterior leaf up to the fifteenth exterior leaf, while insecticides are usually only effective up to the sixth exterior leaf of the head (Trdan et al., 2005; African Entomology 13: 85-95). Therefore, there is an urgent need for cabbage plants which are resistant against this pest.

Although no highly thrips resistant *Brassica oleraceae* varieties are known, huge differences in susceptibility exist among varieties. Certain varieties show an intermediate level of resistance, but no varieties are known that are highly resistant against *Thrips tabaci*. The genetic background of this intermediate resistance against thrips is still poorly understood and it is thought that this is a polygenic trait, inherited as a gene complex in which many genes are involved (Voorrips et al., 2008; Euphytica 163: 409-415).

Citation or identification of any document in this application is not an admission that such document is available as prior art to the present invention.

SUMMARY OF THE INVENTION

Because in the present state of the art no highly thrips resistant cabbage varieties are known, it is the object of the present invention to provide a *Brassica* plants, in particular *Brassica oleracea* plant with a high resistance to *Thrips tabaci*.

In the research that led to the present invention novel *Brassica oleracea* plants were developed that are highly resistant against thrips.

The said resistance of the invention is controlled by a genetic determinant, the inheritance of which is consistent with that of a monogenic additive trait. 'Additive trait' in this case means that the fully achievable resistance is only observable in plants which may comprise the genetic determinant in homozygous state, however plants which may comprise the genetic determinant in heterozygous state will show an intermediate level of resistance.

Since the inheritance of the resistance is comparable to that of a monogenic trait, it has a second advantage over the prior art, because the resistance level is not only higher but also easier to incorporate in new *Brassica* varieties as compared to the complex polygenic traits from the prior art which led to plants with only an intermediate resistance against thrips.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSITS

Seeds of *Brassica oleracea* plants resistant to *Thrips tabaci* were deposited under NCIMB deposit accession number 41760 on 29 Sep. 2010 with NCIMB Ltd. (Ferguson Building, Craibstone Estate, Bucksburn, Aberdeen, AB21 9YA). All seeds of the deposit comprise the genetic determinant homozygously. Plants grown from these seeds are thus highly resistant against *Thrips tabaci*.

The Deposits with NCIMB Ltd, Ferguson Building, Craibstone Estate, Bucksburn, Aberdeen AB21 9YA, UK, under deposit accession number 41760 were made pursuant to the terms of the Budapest Treaty. Upon issuance of a patent, all restrictions upon the deposit will be removed, and the deposit is intended to meet the requirements of 37 CFR §§1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

The present invention thus relates to a *Brassica* plant, in particular a *Brassica oleracea* plant, which may comprise a genetic determinant, which when homozygously present confers high resistance against *Thrips tabaci*, and which is as found in plants grown from seeds of which a representative sample is deposited with the NCIMB under NCIMB accession number 41760.

The present invention also relates to a *Brassica* plant, in particular a *Brassica oleracea* plant, which may comprise the genetic determinant heterozygously, and thus showing intermediate resistance against *Thrips tabaci*, and which genetic determinant is obtainable from plants grown from seeds of which a representative sample is deposited with the NCIMB under NCIMB accession number 41760.

The invention furthermore relates to a *Brassica* plant which may comprise the genetic determinant homozygously, and therefore is highly resistant against *Thrips tabaci*.

In one embodiment the invention provides a *Brassica* plant, in particular a *Brassica oleracea* plant, that is resistant to *Thrips tabaci*, obtainable by crossing a resistant plant of which representative seed was deposited under NCIMB number 41760 with another cabbage plant to produce an F1 and subsequently selfing the F1 to obtain an F2 and selecting a plant therefrom that shows resistance to *Thrips tabaci*.

Furthermore, it was found during the research leading to the present invention that the genetic determinant conferring resistance to *Thrips tabaci*, is located on chromosome 2 and linked to marker BO00200 (SEQ ID NO: 1) and/or marker BO00277 (SEQ ID NO: 2) and/or BO00602 (SEQ ID NO: 5).

More in particular, in the deposit NCIMB 41760 the genetic determinant conferring resistance to *Thrips tabaci*, is located on chromosome 2 between marker BO00458 (SEQ ID NO: 7) and marker BO01225 (SEQ ID NO: 6) and linked to marker BO00200 (SEQ ID NO: 1) and/or marker BO00277 (SEQ ID NO: 2) and/or marker BO00602 (SEQ ID NO: 5).

Figure 1:
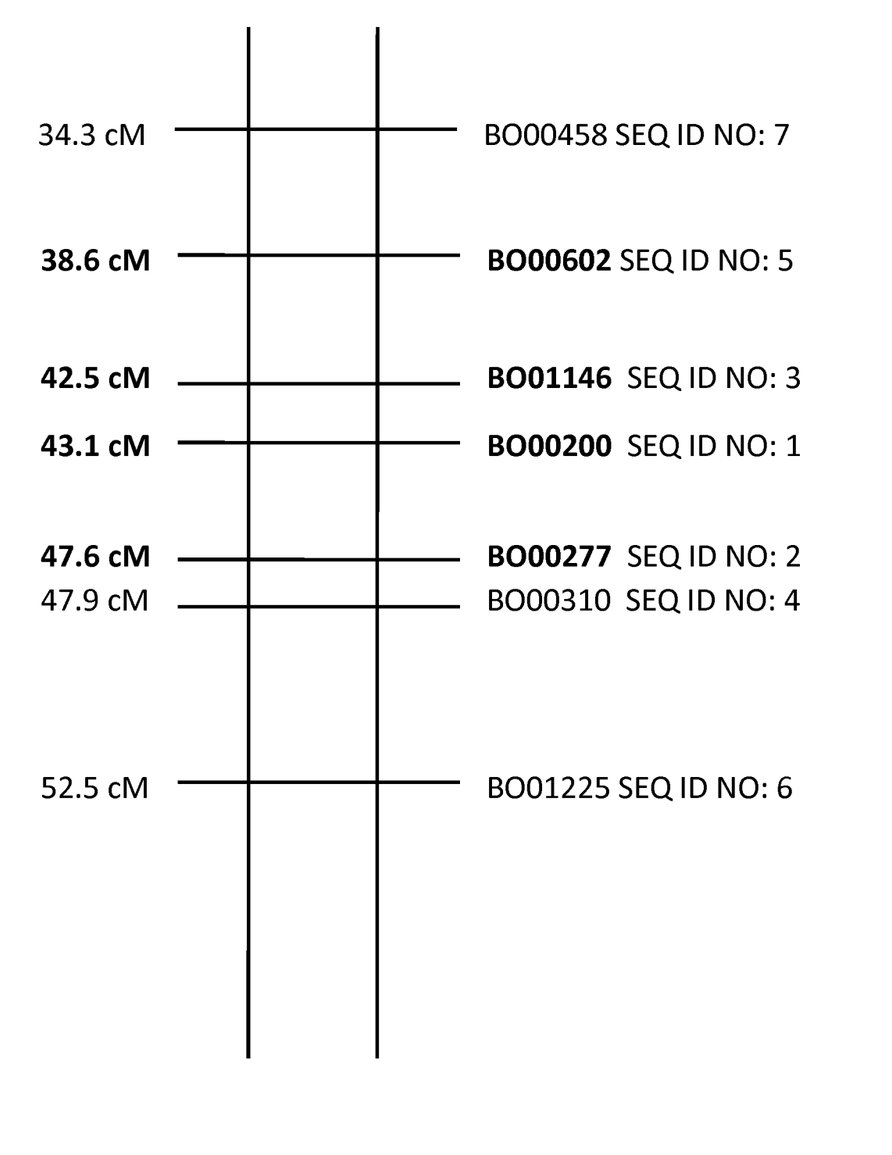
FIG. 1. Schematic overview of a part of chromosome two indicating markers (in bold) that may be linked to the genetic determinant conferring thrips resistance (SEQ ID NO 1, 2, 3, and 5) together with flanking markers (SEQ ID NO: 4, 6, and 7). On the left side the genetic distance indicated in centiMorgans. On the right side, the markers are indicated.

Most in particular the genetic determinant conferring resistance to *Thrips tabaci*, is located on chromosome 2 between marker BO01146 (SEQ ID NO: 3) and marker BO00310 (SEQ ID NO: 4) and linked to marker BO00200 (SEQ ID NO: 1) and/or marker BO00277 (SEQ ID NO: 2) in seeds deposited under NCIMB accession number 41760, see also FIG. 1.

Alternatively the genetic determinant conferring resistance to *Thrips tabaci*, is located on chromosome 2 between markers BO00310 (SEQ ID NO: 4) and BO00458 (SEQ ID NO: 7) and linked to BO00200 (SEQ ID NO: 1) and/or marker BO00277 (SEQ ID NO: 2) and/or marker BO01146 (SEQ ID NO: 3) and/or marker BO00602 (SEQ ID NO: 5), in particular between marker BO00458 (SEQ ID NO: 7) and marker BO01146 (SEQ ID NO: 3) and linked to marker BO00602 (SEQ ID NO: 5).

Therefore, the invention also relates to a *Brassica* plant resistant to *Thrips tabaci*, which may comprise a genetic determinant that confers resistance to *Thrips tabaci*, wherein said genetic determinant is obtainable by introgression from a plant grown from seeds of which a representative sample was deposited with the NCIMB under NCIMB accession number 41760, and wherein the said genetic determinant in the seeds of the seed deposit number NCIMB 41760 is positioned on chromosome 2 and linked to marker BO00200 (SEQ ID NO: 1), and/or BO00277 (SEQ ID NO: 2), and/or marker BO00602 (SEQ ID NO: 5).

A *Brassica* plant carrying the genetic determinant conferring resistance against thrips may suitably be identified among descendants from a cross between a plant susceptible for thrips, and a plant that does carry the genetic determinant in homozygous state, by growing F2 plants from seeds that are the result from the initial cross and a selfing step, and selecting plants showing the desired trait. Selecting the plants may be done phenotypically, or may be done through identification of the genetic determinant, for example by means of one or more of the markers defined herein.

In the absence of molecular markers or in the event that recombination between the molecular markers and the genetic determinant have taken place and thus are not predictive anymore, equivalence of genetic determinants may still be determined by an allelism test. To perform an allelism test, material that is homozygous for the known determinant, a tester plant, is crossed with material that is homozygous for the genetic determinant that is to be tested. This latter plant is referred to as the donor plant. The donor plant to be tested should be or should be made homozygous for the genetic determinant to be tested. The skilled person knows how to obtain a plant that is homozygous for the genetic determinant to be tested. When in the F2 of the cross between a donor plant and a tester plant no segregation for the phenotype related to the genetic determinant is observed, the genetic determinants of the donor plant and the tester plant have been proven to be equivalent or the same.

The invention also relates to a *Brassica* plant that may comprise a genetic determinant conferring resistance to *Thrips tabaci*, wherein plants of first generation progeny (F1) of a cross of the said plant with a tester plant, that may comprise the said genetic determinant and of which representative seed was deposited with the NCIMB under accession number NCIMB 41760, or a progeny plant thereof that may comprise the said genetic determinant, or a plant derived therefrom and which may comprise the said genetic determinant, show a 1:0 segregation for the resistance against *Thrips tabaci*. In both the tester plant and the plant of the invention the genetic determinant is present in homozygous form. Plants of the second and further generations, if obtained by selfing also show a 1:0 segregation for the said resistance pattern. The tester plant may be a plant of which representative seed was deposited with the NCIMB under accession number NCIMB 41760.

The *Brassica* plant of the invention is preferably a *Brassica oleracea* plant, but may also be any other plant of the genus *Brassica* into which the skilled person may introgress the genetic determinant of the invention, e.g. the following *Brassica* species: *Brassica oleracea, Brassica napus, Brassie campestris, Brassica cretica, Brassica rapa, Brassica juncea*, and *Brassica nigra*. The skilled person knows how to make interspecific crosses with these species, e.g. by means of embryo rescue, protoplast fusion, and other related technologies.

In another embodiment the invention relates to seeds which may comprise the said genetic determinant conferring resistance against *Thrips tabaci*. A plant grown from the seeds is highly resistant to thrips when the genetic determinant is present in homozygous state.

The invention thus further relates to seeds which may comprise said genetic determinant and which seeds are capable of growing into plants that are highly resistant against *Thrips tabaci*.

According to a further aspect thereof, the invention relates to propagation material capable of growing into a plant of the invention.

In one embodiment, such propagation material is formed by seed of a *Brassica* plant of the invention, wherein the plant that may be grown from the seed may comprise a genetic determinant of the invention.

In another embodiment the propagation material capable of growing into a plant of the invention is selected from the group consisting of microspores, pollen, ovaries, ovules, embryos, embryo sacs, egg cells, cuttings, roots, root tips, hypocotyls, cotyledons, stems, leaves, flowers, anthers, seeds, meristematic cells, protoplasts, and cells.

In a further embodiment the invention relates to tissue culture of propagation material capable of growing into a plant of the invention.

Suitably, the plant produced from the propagation material may comprise the genetic determinant as found in *Brassica* plants grown from seeds of seed lot AG6359-35/39, a representative sample of which was deposited with the NCIMB under NCIMB accession number 41760. When the genetic determinant is present in homozygous state the plant produced shows high resistance to *Thrips tabaci*, in particular the resistance as observed in *Brassica* plants grown from seeds of seed lot AG6359-35/39, a representative of which was deposited with the NCIMB under NCIMB accession number 41760. When the genetic determinant is present in heterozygous state the plant shows intermediate resistance.

The invention also relates to progeny of the plants, cells, tissues and seeds of the invention. Such progeny may in itself be plants, cells, tissues or seeds.

As used herein the word "progeny" is intended to mean the first and all further descendants from a cross with a plant of the invention that may comprise the said genetic determinant. "Progeny" also encompasses plants that carry the trait of the invention and are obtained from other plants or progeny of plants of the invention by vegetative propagation or multiplication.

Therefore, in one embodiment the invention relates to progeny of a *Brassica* plant which may comprise the genetic determinant of the invention.

In a further embodiment the invention relates to progeny of *Brassica* plants of the invention that are resistant against *Thrips tabaci*. These progeny plants thus may comprise the genetic determinant conferring resistance against thrips.

In one aspect the invention relates to the harvested part of a *Brassica* plant which may comprise the genetic determinant conferring thrips resistance.

The invention furthermore relates to a food product which may comprise one or more harvested parts of a *Brassica* plant which may comprise the genetic determinant conferring thrips resistance.

The harvested part or food product may be or may comprise a cabbage head, a curd, a stem, a leaf, a root, a sprout, a seed, or any other part of a *Brassica* plant. The harvested part may also be used for the production of bio-fuel. The food product or harvested part, may have undergone one or more processing steps. Such a processing step might comprise but is not limited to any one of the following treatments or combinations thereof: cutting, washing, cooking, steaming, baking, frying, pasteurizing, freezing, grinding, extracting oil, pickling, or fermenting. The processed form that is obtained is also part of this invention.

Another aspect of this invention relates to a nucleic acid molecule which is causative of resistance against *Thrips tabaci*. The said DNA molecule may comprise a DNA sequence which is positioned on chromosome 2 between markers BO00458 (SEQ ID NO: 7) and BO01225 (SEQ ID NO: 6), more in particular between markers BO00458 (SEQ ID NO: 7) and BO00146 (SEQ ID NO: 3), or between markers BO00146 (SEQ ID NO: 3) and BO00310 (SEQ ID NO: 4), or a part thereof.

Yet another aspect of the invention relates to use of the markers and said nucleic acid molecule to identify plants which are resistant against *Thrips tabaci*, and/or carry the genetic determinant conferring resistance to *Thrips tabaci*.

Therefore, in one embodiment the invention relates to the use of marker BO00200 (SEQ ID NO: 1), or marker BO00277 (SEQ ID NO: 2), or marker BO00602 (SEQ ID NO: 5), or the said DNA molecule which may comprise a DNA sequence which is positioned on chromosome 2 between markers BO00458 (SEQ ID NO: 7) and BO01225 (SEQ ID NO: 6), or BO00146 (SEQ ID NO: 3) and BO00310 (SEQ ID NO: 4), or BO00458 (SEQ ID NO: 7) and BO00146 (SEQ ID NO: 3), or part thereof, to identify plants resistant against *Thrips tabaci*, and/or carrying the genetic determinant conferring resistance to *Thrips tabaci*.

The skilled person knows how to develop new markers linked to a trait using already known markers, QTLs, alleles, genes or other DNA molecules that are associated with a certain trait.

Thus, the invention also relates to the use of markers BO00200 (SEQ ID NO: 1), BO00277 (SEQ ID NO: 2), and BO00602 (SEQ ID NO: 5), and the said DNA molecule, or part thereof, for developing other markers linked to the genetic determinant conferring thrips resistance.

In one embodiment, the genetic determinant conferring resistance to *Thrips tabaci* also confers resistance against other sap sucking insect species, wherein the sap sucking insect species is selected from, but not limited to the group consisting of *Aleyrodes proletella, Myzus persicae*, and *Brevicoryne brassicae*.

In one aspect the invention relates to a process for producing *Brassica* plants which may comprise a genetic determinant that confers resistance to *Thrips tabaci*, which may comprise the step of selecting said *Brassica* plants from a population of *Brassica* plants segregating for the said genetic determinant using marker BO00200 (SEQ ID NO: 1) and/or marker BO00277 (SEQ ID NO: 2) and/or BO00602 (SEQ ID NO: 5).

The term 'genetic determinant' as used herein encompasses one or more QTLs, genes, or alleles. These terms are used interchangeably. A genetic determinant may be identified by the use of a molecular marker. A genetic determinant may alternatively be identified by the position on a genetic map, or by indication of the location on a linkage group or chromosome. When a genetic determinant is not linked to a specific molecular marker any longer, but its position on a chromosome as defined on a genetic map is unaltered, this genetic determinant is still the same as when it was linked to the molecular marker. The genetic trait that it confers is therefore also still the same. The 'genetic trait' is the trait or characteristic that is conferred by the genetic determinant. The genetic trait may be identified phenotypically, for example by performing a bio-assay. However, also plant stages for which no phenotypic assay may be performed do carry the genetic information that leads to the genetic trait. 'Trait' or 'phenotypic trait' may be used instead of 'genetic trait'.

In one embodiment, the invention relates to *Brassica* plants of the invention that carry the genetic determinant conferring resistance to *Thrips tabaci*, and having acquired said determinant by introduction of the genetic information that is responsible for the trait from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a noncrossable species or a synthetic gene.

The invention also relates to the germplasm of plants of the invention. The germplasm is constituted by all inherited characteristics of an organism and according to the invention encompasses at least the genetic determinant of the invention. The germplasm may be used in a breeding program for the development of thrips resistant *Brassica* plants.

In one aspect the invention relates to a method for production of a *Brassica* plant is resistant against *Thrips tabaci*, which may comprise:
  a) crossing a plant which may comprise a genetic determinant that leads to resistance against *Thrips tabaci* with another plant;
  b) selfing the resulting F1 for obtaining F2 plants;
  c) selecting plants resistant to *Thrips tabaci* in the F2;
  d) optionally performing one or more additional rounds of selfing or crossing, and subsequently selecting, for a plant which may comprise said resistance against *Thrips tabaci*.

It is clear that the parent that provides the trait of the invention is not necessarily a plant grown directly from the deposited seeds. The parent may also be a progeny plant from the seed or a progeny plant from seeds that are identified to have the trait of the invention by other means.

In one aspect, the invention relates to a method for production of a *Brassica* plant resistant against *Thrips tabaci*, which may comprise:
  a) crossing a plant which may comprise the genetic determinant that leads to resistance against *Thrips tabaci* with another plant;
  b) optionally backcrossing the resulting F1 with the preferred parent;
  c) selecting for plants resistant to *Thrips tabaci* in the F2;
  d) optionally performing one or more additional rounds of selfing or crossing, and subsequently selecting, for a plant which may comprise the said resistance is performed.

The invention additionally provides a method of introducing a desired trait into a *Brassica* plant resistant against *Thrips tabaci*, which may comprise:
  a) crossing a *Brassica* plant resistant to *Thrips tabaci*, representative seed of which were deposited with the NCIMB under deposit number NCIMB 41760, with a second *Brassica* plant that may comprise a desired trait to produce F1 progeny;
  b) selecting an F1 progeny that may comprise said resistance and the desired trait;
  c) crossing the selected F1 progeny with either parent, to produce backcross progeny;
  d) selecting backcross progeny which may comprise the desired trait and resistance against *Thrips tabaci*; and
  e) optionally repeating steps c) and d) one or more times in succession to produce selected fourth or higher backcross progeny that may comprise the desired trait and resistance against *Thrips tabaci*. The invention includes a *Brassica* plant produced by this method.

In one embodiment selection for plants resistant against *Thrips tabaci* is done in the F1 by using marker BO00200 (SEQ ID NO: 1) and/or marker BO00277 (SEQ ID NO: 2) and/or BO00602 (SEQ ID NO: 5). In another aspect selection for the trait of the invention is started in the F2 of a cross or alternatively of a backcross. Selection of plants in the F2 can be done phenotypically as well as by using the said markers.

In one embodiment selection for plants resistant against *Thrips tabaci* is started in the F3 or a later generation.

In one embodiment the plant which may comprise the genetic determinant is a plant of an inbred line, a hybrid, a doubled haploid, or of a segregating population.

The invention further provides a method for the production of a *Brassica* plant resistant against *Thrips tabaci* by using a doubled haploid generation technique to generate a doubled haploid line which may comprise the said resistance.

The invention furthermore relates to hybrid seed that may be grown into a thrips resistant plant and to a method for producing such hybrid seed which may comprise crossing a first parent plant with a second parent plant and harvesting the resultant hybrid seed, wherein said first parent plant and/or said second parent plant is the plant as claimed.

In one embodiment, the invention relates to a method for producing a hybrid Brassica plant that is resistant to thrips, which may comprise crossing a first parent Brassica plant with a second parent Brassica plant and harvesting the resultant hybrid seed, of which the first parent plant and/or the second parent plant is resistant against Thrips tabaci, and growing said hybrid seeds into thrips resistant hybrid plants.

The invention also relates to a method for the production of a Brassica plant resistant against Thrips tabaci by using a seed that may comprise a genetic determinant in its genome that leads to resistance against Thrips tabaci for growing the said Brassica plant. The seeds are suitably seeds of which a representative sample was deposited with the NCIMB under deposit number NCIMB 41760.

The invention also relates to a method for seed production which may comprise growing Brassica plants from seeds of which a representative sample was deposited with the NCIMB under deposit number NCIMB 41760, allowing the plants to produce seeds, and harvesting those seeds. Production of the seeds is suitably done by crossing or selfing.

In one embodiment, the invention relates to a method for the production of a Brassica plant resistant against Thrips tabaci by using tissue culture.

The invention furthermore relates to a method for the production of a Brassica plant resistant against Thrips tabaci by using vegetative reproduction.

In one embodiment, the invention relates to a method for the production of a Brassica plant resistant against Thrips tabaci by using a method for genetic modification to introgress the said resistance into the Brassica plant. Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant.

The invention also relates to a breeding method for the development of Brassica plants that are resistant against Thrips tabaci wherein germplasm which may comprise said resistance is used. Representative seed of said plant which may comprise the genetic determinant and being representative for the germplasm was deposited with the NCIMB under deposit number NCIMB 41760.

In a further embodiment the invention relates to a method for the production of a Brassica plant resistant against Thrips tabaci wherein progeny or propagation material of a plant which may comprise the genetic determinant conferring said resistance is used as a source to introgress the said resistance into another Brassica plant. Representative seed of said plant which may comprise the genetic determinant was deposited with the NCIMB under deposit number NCIMB 41760.

The invention provides preferably a Brassica plant resistant to Thrips tabaci, which plant is obtainable by any of the methods herein described and/or familiar to the skilled person.

SEQUENCE DATA

TABLE 1

Sequence data of the SNP markers of FIG. 1. In NCIMB deposit 41760 the markers B000200, B000277, and B000602 are linked to the genetic determinant conferring resistance against Thrips.

| | |
|---|---|
| B000200 SEQ ID NO: 1 | TTGTCCGGAAAATAAGCCCTTCCTTCTCCATGAGCCGCCCAA ACTCCTAAAGTACTTACC[T/C]TCCATTCCTTTCAGCACTATTG ACGGACAGTCCTTGATGGTCACGCTTGTGAACCTGCAG |
| B000277 SEQ ID NO: 2 | GCTTGTCCAGCTTATGAGCATTTTGTAATACATGTTTGCTTGG ATGGTCAAACCTGAAAA[A/C]ACACACAAGTTCAACAATTCT CAGAAGATGGATAAACCTGCAG |
| B001146 SEQ ID NO: 3 | TTAAAAACAAATNATGTTTTGTTTTACCTGCTTTTTCCTCTTCT CGCTNNTTGNCAGCTTCTTCTCTCTGTTGGCGAATCAGAGCCA AACGATCTGTACACAAACACACACAAGGGATAAGATAATCA A[A/*]TAGGCTCATCTGGTAACAAAGAAAGAGAACAAGAGGT CCATTGTTTTTTTACNNAANTCCTTNNTTGNTTGCTCGGTTTT NNCNTGNNNCTGCAACCTCATGTATCGCTCATGAGCTCGTTG CTTCTCTAGCTCCTCCCTGCAG |
| B000310 SEQ ID NO: 4 | CATGTCATCTTTCGTNAGGTTTGTTATTTCTATGCCTCGTTTG AGAGCTTCCCTCAATGG[A/C]CCCATAGTTGCATCTTTCACTA GGTTCTTCATGTCTGATCCCGAGTACCCTGCAG |
| B000602 SEQ ID NO: 5 | TTAAATATGTGAATGCTGAAATRTTTGTTTAGCAGA[C/G]GAG ACACAGGAAGAAGATCATCTCATGTTGTTCGCTCTCTCAGCA GAGAGTTTGAAGTTGCAAGTACTCCTGCAG |
| B001225 SEQ ID NO: 6 | CCCTGTTWAAGGAGCCTCCTTGGAGCTTGTTGATACCTCAAA GTTAGGTAGTGACAATGTGGATAATGAAAGTTTGAAGCTT T[A/C]TCAACAATTAGCTGATAAGAGAGGTTCTTGTGAAGAGGA TTTGATGAGAATCTCTATGAAGAAACGAGGTGTAATCAGCAA TGTCTCCACCTCTYTGATGGAARATGCTRGTTTYGATGGAAT ATTGGCTTCTCCTGCAG |
| B000458 SEQ ID NO: 6 | TAAAGAACCTGATGAAGAAAGTGAAGAGCTAGGTGGAAACC TACTTGACCTGCTCCTAAG[T/G]TTCTTCACTTCCGGGATCTTC TCCTCTTTTGATCTCACCTGCCTCACCTTTGCCTCGTTC |

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Thrips resistant plants of the invention were compared with susceptible plants and plants with an intermediate resistance in an open field trial. Plants were naturally infected by using an attractant species. In this trial leek plants were used as a natural attractant for thrips. For the skilled person it is known that also other plants can be used as an attractant for *Thrips tabaci*, such as onion or shallots.

Plants from variety Rinda and Hurricane were used in this trial as susceptible control plants. Plants from varieties Langendijker Bewaar, Tacoma, and Multima were included in this trial since they are known to be intermediately resistant against *Thrips tabaci*. As highly resistant plants of the invention, plants grown from seeds of seed lot AG6359-35/39 of which a representative sample was deposited with the NCIMB under NCIMB accession number 41760, as well as plants of three lines derived from plants grown from seed of the seed deposit that were selfed, were used. These lines are AG2971, AG2973, and AG3086.

Each plant was scored for the amount of thrips infestation, based on the scale explained in Table 2. Symptoms were scored when the cabbage heads were mature. The skilled person is not bound to using this scale but can also use a scale with another subdivision of categories as long as the scoring will be done at the same stage, i.e. when the cabbage head is mature. This is not of influence on the final result of the screening.

TABLE 2

Scoring of thrips infestation.

| Score | Symptoms | |
|---|---|---|
| 1 | No symptoms/no damage | High resistance |
| 2 | Occasional small symptoms on outer leaves | |
| 3 | Minor damage. Max. 20% of head's surface is covered by symptoms, only outer leaves are infected. | Intermediate resistance |
| 4 | Medium damage. Max. 50% of the head's surface (all leaves accumulated) is covered by symptoms. The symptoms are max. in the second and third layer. | |
| 5 | Heavy damage. More than 50% of the head's surface (all leaves accumulated) is covered by symptoms. Damage also observed in deeper leaf layers | Susceptible |

In Table 3 the scores of the trial are summarized. It is clear that all plants of the invention display a significantly higher resistance against thrips.

In field trials with a high disease pressure, even highly resistant plants show occasional symptoms of thrips infection. This can e.g. be the case when attractant plant species are used. In order to make a fair comparison between different trials using natural infection the same comparison varieties should be used, because the relative differences in damage observed by thrips infestation will approximately be the same while the mean scores of same plants in different trials can deviate substantially.

TABLE 3

Score of thrips resistance field trial.

| Material | Number of plants screened | Mean score | |
|---|---|---|---|
| AG6359-35/39 (NCIMB 41760) | 17 | 1 | Resistant |
| AG2971 | 14 | 1.1 | Resistant |
| AG2973 | 16 | 1.2 | Resistant |
| AG3086 | 4 | 1.2 | Resistant |
| Langendijker Bewaar | 22 | 3.1 | Intermediate |
| Tacoma | 6 | 3 | Intermediate |
| Multima | 6 | 3 | Intermediate |
| Hurricane | 10 | 4.4 | Susceptible |
| Rinda | 10 | 5 | Susceptible |

Example 2

Transfer of Thrips Resistance to Susceptible Plants

A thrips resistant plants of the invention AG 2973-35 (see Table 2 for resistance scores), was crossed with a susceptible plant FM 2979-01. Plants of the F1 were observed in a field trial as described in Example 1. No highly thrips resistant plants were observed.

From the F1 population a plant was selected which was selfed to obtain a population of F2 plants. The F2 was placed in a field trial as described in Example 1. Resistance scores are summarized in Table 4.

The segregation of the F2 population demonstrates that the inheritance of the resistance of the invention is comparable with that of a monogenic additive trait (highly resistant: intermediate resistant: susceptible=1:2:1). Depending on the genetic background of the susceptible parent plant there can be a different distribution between intermediately resistant and susceptible plants observed in the F2.

TABLE 4

| F2 population | Resistant plants | Intermediately resistant plants | Susceptible plants | Chi-square |
|---|---|---|---|---|
| F2(AG 2973-35 × FM 2979-01) | 24 | 59 | 32 | 1.24 |

The invention is further described by the following numbered paragraphs:

1. A *Brassica* plant in particular a *Brassica oleracea* plant comprising a genetic determinant, which when homozygously present confers high resistance against *Thrips tabaci*, and which is as found in plants grown from seeds of which a representative sample is deposited with the NCIMB under NCIMB accession number 41760.

2. A *Brassica* plant of paragraph 1, which is homozygous for the genetic determinant and resistant against *Thrips tabaci*.

3. The *Brassica* plant of paragraph 1 or paragraph 2, wherein the said genetic determinant in the seeds of NCIMB deposit 41760 is located on chromosome 2 and linked to marker BO00200 (SEQ ID NO: 1) and/or marker BO00277 (SEQ ID NO: 2) and/or marker BO00602 (SEQ ID NO: 5).

4. Seed comprising the genetic determinant as defined in any one of the paragraphs 1 to 3.

5. Seed of paragraph 4, wherein the plant that can be grown from the seed is resistant to *Thrips tabaci*.

6. Progeny of a *Brassica* plant of anyone of the paragraphs 1 to 3 or progeny of plants grown from seeds of paragraph 4 or paragraph 5, wherein the plant comprises the genetic determinant as defined in any one of the paragraphs 1-3.

7. Progeny plant of paragraph 6 wherein the progeny plant is resistant against *Thrips tabaci*.

8. Propagation material derived from a plant of any one of the paragraphs 1 to 3, wherein the propagation material comprises the genetic determinant as defined in any one of the paragraph 1 to 3.

9. Propagation material capable of growing into a plant as claimed in any one of the paragraphs 1 to 3.

10. Propagation material of paragraph 8 or paragraph 9, wherein the propagation material is selected from the group consisting of microspores, pollen, ovaries, ovules, embryos, embryo sacs, egg cells, cuttings, roots, root tips, hypocotyls, cotyledons, stems, leaves, flowers, anthers, seeds, meristematic cells, protoplasts, and cells.

11. Tissue culture of propagation material of any one of the paragraphs 8 to 10.

12. Harvested part of a *Brassica* plant of any one of the paragraphs 1-3, 6 or 7, which harvested part is in particular selected from the group consisting of cabbage head, curd, stem, leaf, sprout, root and seed, optionally in processed form.

13. Harvested part of paragraph 12, wherein the harvested part is a food product.

14. A nucleic acid molecule causative of resistance against *Thrips tabaci*, comprising a DNA sequence, which is linked to marker BO00200 (SEQ ID NO: 1) and/or marker BO00277 (SEQ ID NO: 2) and/or BO00602 (SEQ ID NO: 5) located on chromosome 2, in particular located on chromosome 2 between marker BO00458 (SEQ ID NO: 7) and marker BO01225 (SEQ ID NO: 6), or a resistance conferring part of said nucleic acid molecule.

15. Use of the markers as defined in paragraph 3, and/or use of the nucleic acid molecule of paragraph 14, to identify or develop *Thrips tabaci* resistant plants, or develop other markers linked to the genetic determinant as defined in anyone of the paragraphs 1 to 3.

16. Use of the markers of paragraph 2, or use of the nucleic acid molecule of paragraph 13, to develop other markers linked to the genetic determinant as defined in paragraph 2.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

---

What is claimed is:

1. A *Brassica oleracea* plant comprising a genetic determinant, which when homozygously present confers high resistance against *Thrips tabaci*, and which is as found in plants grown from seeds of NCIMB accession number 41760, wherein high resistance comprises no symptoms, no damage or occasional small symptoms of thrips infection on outer leaves of a mature cabbage head of a plant exposed to *Thrips tabaci*; wherein the said genetic determinant in the seeds of NCIMB 41760 is located on chromosome 2 and linked to marker BO00200 (SEQ ID NO: 1) and/or marker BO00277 (SEQ ID NO: 2) and/or BO00602 (SEQ ID NO: 5).

2. The plant as claimed in claim 1, which is homozygous for the genetic determinant and resistant against *Thrips tabaci*.

3. A *Brassica oleracea* seed comprising the genetic determinant as defined in claim 1.

4. The seed as claimed in claim 3, wherein the plant grown from the seed is resistant to *Thrips tabaci*.

5. A progeny of the plant of claim 1, wherein the progeny comprises the genetic determinant, which when homozygously present confers high resistance against *Thrips Tabaci*, and which is as found in plants grown from seeds of NCIMB accession number 41760, wherein high resistance comprises no symptoms, no damage or occasional small symptoms of thrips infection on outer leaves of a mature cabbage head of a plant exposed to *Thrips tabaci*.

6. The progeny as claimed in claim 5 wherein the progeny is resistant against *Thrips tabaci*.

7. A propagation material derived from the plant as claimed in claim 1, wherein the propagation material comprises the genetic determinant as defined in claim 1.

8. A propagation material capable of growing into the plant as claimed in claim 1, wherein said propagation material comprises the genetic determinant as defined in claim 1.

9. The propagation material as claimed in claim 7 or claim 8, wherein the propagation material comprises a microspore, pollen, ovary, ovule, embryo, embryo sac, egg cell, cutting, root, root tip, hypocotyl, cotyledon, stem, leaf, flower, anther, seed, meristematic cell, protoplast or cell.

10. A tissue culture of the propagation material as claimed in claim 8, wherein said tissue culture comprises the genetic determinant as defined in claim 1.

11. A harvested part of the plant as claimed in claim 1, which harvested part comprises a cabbage head, curd, stem, leaf, sprout, root or seed, wherein said harvested part comprises the genetic determinant as defined in claim 1.

12. The harvested part as claimed in claim 11, wherein the harvested part is a food product.

13. A method of producing of a *Brassica oleracea* plant resistant against *Thrips tabaci*, comprising:
a) crossing a *Brassica oleracea* plant comprising the genetic determinant of claim 1 that leads to resistance against *Thrips tabaci* with another *Brassica oleracea* plant;
b) selfing or backcrossing the resulting F1 for obtaining F2 plants;
c) selecting plants resistant to *Thrips tabaci* in the F2; and
d) optionally performing one or more additional rounds of selfing or crossing, and subsequently selecting, for a plant comprising said resistance against *Thrips tabaci*, wherein said plant comprises said genetic determinant.

14. A method for producing a hybrid *Brassica oleracea* plant that is resistant to thrips, comprising crossing a first parent *Brassica oleracea* plant with a second parent *Brassica oleracea* plant and harvesting the resultant hybrid seed, wherein the first parent plant and/or the second parent plant comprises the genetic determinant of claim 1 and is resistant against *Thrips tabaci*, and growing said hybrid seeds into thrips resistant hybrid plants.

15. The method of claim 13 wherein the genetic determinant, which when homozygously present confers high resistance against *Thrips tabaci*, is as found in plants grown from seeds of NCIMB accession number 41760, wherein high resistance comprises no symptoms, no damage or occasional small symptoms of thrips infection on outer leaves of a mature cabbage head of a plant exposed to *Thrips tabaci*.

16. The method of claim 14, wherein the first parent plant or the second parent plant comprises a genetic determinant, which when homozygously present confers high resistance against *Thrips tabaci*, and which is as found in plants grown from seeds of NCIMB accession number 41760, wherein high resistance comprises no symptoms, no damage or occasional small symptoms of thrips infection on outer leaves of a mature cabbage head of a plant exposed to *Thrips tabaci*.

* * * * *